United States Patent [19]
Sano et al.

[11] Patent Number: 5,287,129
[45] Date of Patent: Feb. 15, 1994

[54] FUNDUS CAMERA

[75] Inventors: Eiichi Sano; Hiroshi Minegishi, both of Tokyo, Japan

[73] Assignee: Kabushiki Kaisha Topcon, Tokyo, Japan

[21] Appl. No.: 786,467

[22] Filed: Nov. 4, 1991

[30] Foreign Application Priority Data

Nov. 5, 1990 [JP] Japan .................. 2-297258

[51] Int. Cl.⁵ .................. A61B 3/02; A61B 3/14; G02B 5/22
[52] U.S. Cl. .................. 351/233; 351/206; 351/213; 359/385; 359/889
[58] Field of Search .................. 351/206–221, 351/233–235, 243, 246; 359/368, 379–389, 885, 889–891; 354/62

[56] References Cited

U.S. PATENT DOCUMENTS

| 3,799,645 | 3/1974 | Stankewitz | 359/388 |
| 4,512,640 | 4/1985 | Nihoshi | 359/381 |
| 4,717,952 | 1/1988 | Kohayakawa et al. | 351/206 |
| 4,799,783 | 1/1989 | Takahashi et al. | 351/206 |
| 5,118,179 | 6/1992 | Sano et al. | 351/207 |

Primary Examiner—Bruce Y. Arnold
Assistant Examiner—Thong Nguyen
Attorney, Agent, or Firm—Finnegan, Henderson, Farabow, Garrett & Dunner

[57] ABSTRACT

This invention concerns a fundus camera which can take photographs other than by fluorescence or by fluorescence. An optical device is withdrawn from the optical path of a photographic system at the same time as a barrier filter for taking photographs by fluorescence is inserted and is inserted in the optical path of the photographic system for observation purposes at the same time as the barrier filter is removed. The optical device has the same optical path length as the barrier filter, and thus a focused fundus image attained during observation is not upset when fluorescent photographs are taken.

9 Claims, 3 Drawing Sheets

FUNDUS CAMERA

BACKGROUND OF THE INVENTION

1. Field of the Invention

This invention concerns the improvement of a fundus camera which can take photographs other than by fluorescence, by fluorescence under visible light, and by fluorescence under infra-red light.

2. Description of the Prior Art

Conventionally, a fundus camera is known which can take photographs other than by fluorescence, by fluorescence under visible light, and by fluorescence under infra-red light. In this fundus camera, when taking photographs by fluorescence after completing observations to determine the part to be photographed, a photographic switch is operated. Due to the operation of this switch, an exciter filter for fluorescent photography is inserted in the optical path of an illuminating optical system before a flash tube operates. When the flash tube operates, the fundus of the subject's eye is irradiated by illuminating light of specific wavelengths. The subject has previously been given an injection of a fluorescent agent. After a certain time has elapsed, blood containing this fluorescent agent flows into the blood vessels of the subject's eye, and emits fluorescence under the illuminating light of specific wavelengths. A barrier filter for fluorescent photography is also inserted in the photographic optical system in synchronism with the exciter filter. Fluorescence from the fundus is then guided through this barrier filter to a photographic means, and a satisfactory image of the fundus is thus obtained.

However, the concentration of fluorescent agent in the blood is low immediately before it flows into the blood vessels of the fundus. Subsequently it rises, and then falls as blood flows through the small vessels. As a result, the brightness of the fluorescence increases in a first stage, remains constant in a middle stage, and decreases in a later stage. While the barrier filter for fluorescent photography is inserted in the photographic optical system when making fluorescent observations in the later stage, the image of the subject's eye is dark, and it is impossible to carry out proper alignment and focusing of the system. When making observations in the fluorescent photographic mode, therefore, the barrier filter is removed from the photographic optical system if the image of the eye is dark in order to carry out proper focusing and alignment. The photographic switch is then operated, the barrier filter for fluorescent photography is inserted in the photographic optical system in synchronism with, for example, the action of a shutter, the flash tube is operated, and a photograph by fluorescence is taken.

In this fundus camera, however, no provision is made for the change in the length of the optical path when the barrier filter is inserted or removed from the photographic optical system. Even if, a properly focused image of the fundus is obtained when making observations, therefore, it is impossible to obtain a properly focused photographic image.

SUMMARY OF THE INVENTION

It is therefore an object of the invention to provide a fundus camera wherein, once the fundus has been properly focused for observation, the focus is not upset when the barrier filter for fluorescent photography is inserted in or removed from the optical path of the photographic optical system.

To resolve this problem, this invention provides a fundus camera which can take photographs other than by fluorescence or by fluorescence, wherein an optical device is provided which is removed from the optical path of the photographic system at the same time as the barrier filter is inserted, and inserted in the optical path of the photographic system at the same time as the barrier filter is removed, in order to correct the length of the optical path.

As the fundus camera of this invention has the above construction, once a properly focused image of the fundus has been obtained for observation purposes, the focusing is not upset when taking photographs by fluorescent light. It is therefore unnecessary to re-focus the camera, and its operation can be simplified.

BRIEF DESCRIPTION OF THE DRAWINGS

FIG. 1 is a schematic diagram of the optical system of the camera;

FIG. 2 is an overall inclined view of the camera;

FIG. 3 is a schematic diagram of the operating section of the camera.

DESCRIPTION OF THE PREFERRED EMBODIMENTS

An embodiment of the fundus camera of this invention will now be described with reference to the drawings.

Figure 2:
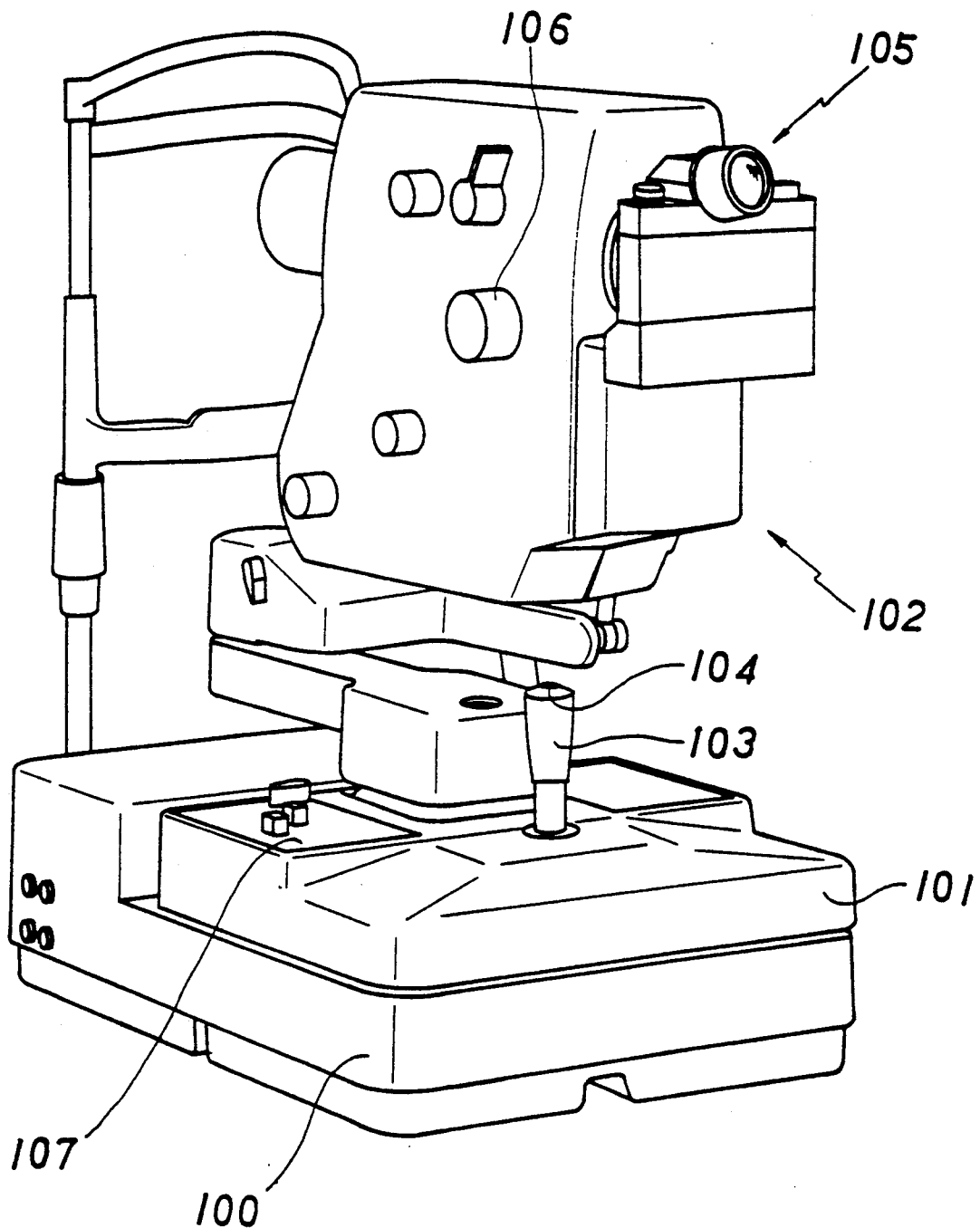

In FIG. 2, 100 is a fixed base, 101 is a mounting platform, 103 is a joy-stick and 104 is a photographic switch. By moving the joy-stick 103 forwards, backwards and to the left or to the right, the mounting platform 101 can be moved back and forth or to left and right of the subject. The operator performs an alignment using the joy-stick 103, and observes the fundas of the subject's eye through an eyepiece 105. A focusing adjustment control 106 is provided on the side of the apparatus chassis 102 so as to permit focusing. A control panel 107 is also provided on the upper surface of the mounting platform 101.

Figure 1:
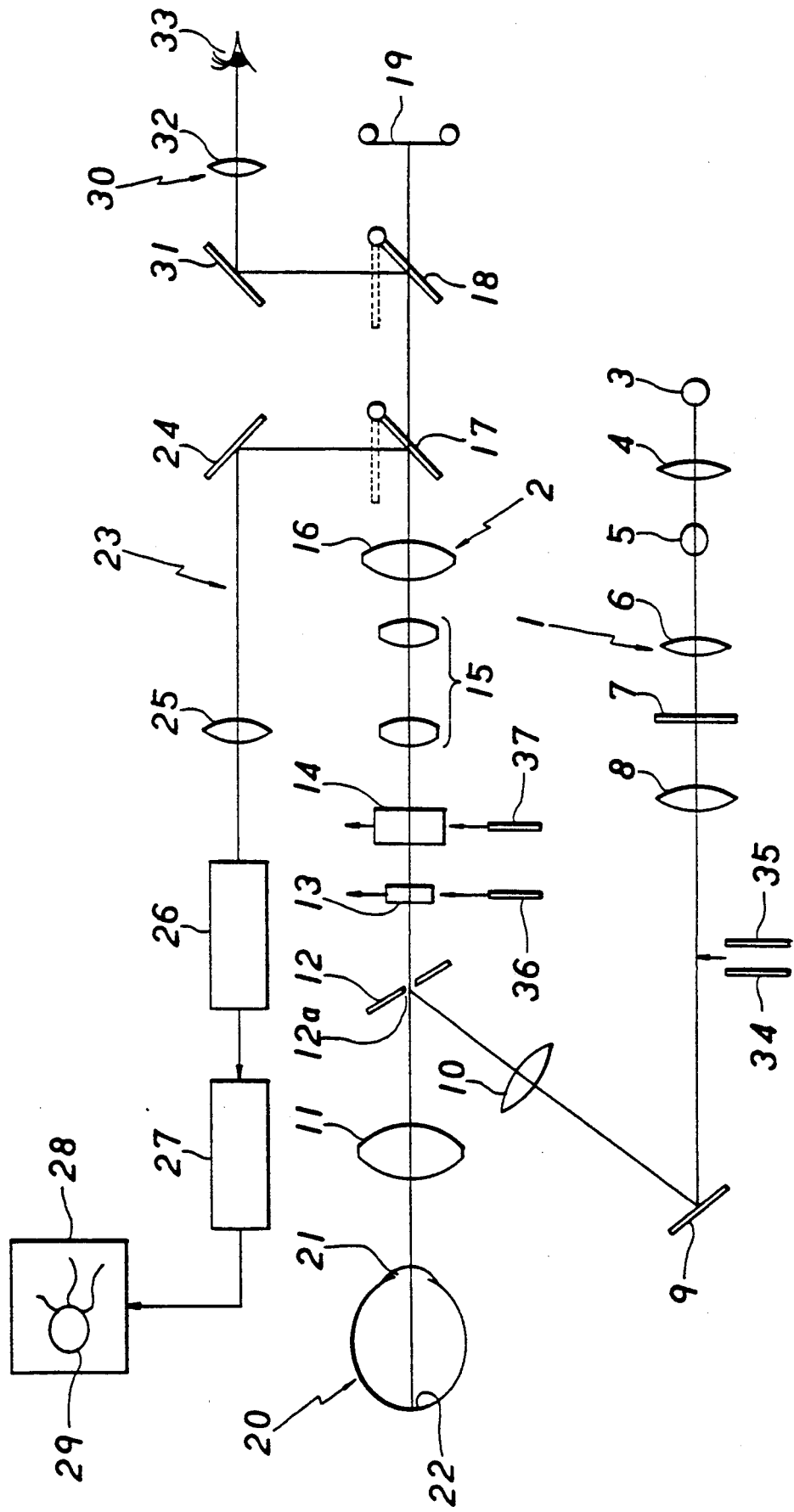
FIGS. 1-3 are drawings illustrating one embodiment of the fundus camera of this invention.

The apparatus chassis 102 contains an optical system of the type shown in FIG. 1. In FIG. 1, 1 is an illuminating optical system and 2 is a photographic optical system. The illuminating optical system 1 essentially comprises a halogen lamp 3 as an observation light source, a condensing lens 4, a xenon lamp 5 as a photographic light source, a condensing lens 6, an annular diaphragm 7, a relay lens 8, a mirror 9 and a relay lens 10.

The photographic optical system 2 essentially comprises an objective lens 11, a holed mirror 12, optical devices 13, 14 for correcting the length of the optical path, a focusing lens 15, an imaging lens 16, a path switching mirror 17, a quick return mirror 18 and a film 19. The objective lens 11 is positioned facing the subject's eye. The annular diaphragm 7 is situated in a conjugate position to the pupil 21 of the subject's eye 20 with respect to the relay lenses 8 and 10, and the objective lens 11. The optical devices 13, 14 for correcting the optical path length are situated between the holed mirror 12 and the focusing lens 15. These path length correcting devices 13, 14 are withdrawn from the optical path of the photographic system 2 at the same time as the barrier filter for taking photographs by fluorescence is inserted in the path, and are inserted in the path at the same time as the barrier filter is withdrawn from same.

When making observations, illuminating light from the halogen lamp 3 passes via the condensing lenses 4 and 6, the annular diaphragm 7, the relay lens 8, the mirror 9, the relay lens 10, the holed mirror 12 and the objective lens 11 to the subject's eye 20. The fundus 22 of the subject's eye is thereby illuminated. When the illuminating light passes through the pupil 21 of the subject's eye 20, it becomes ring-shaped. When taking photographs, the xenon lamp 5 is switched on by the photographic switch 104 as shown in FIG. 2, and the fundus 22 is illuminated in the same way.

The light beam from the fundus 22 is guided via the objective lens 11 to the holed mirror 12, and passes via the hole 12a of the holed mirror 12, the focusing lens 15 and the imaging lens 16 to the path switching mirror 17. The path switching mirror 17 is inserted in or withdrawn from the optical path of the photographic optical system 2 by the action of a switching mirror drive means, not shown. When making observations through the eyepiece or recording on film, the path switching mirror 17 is withdrawn from the optical path of the photographic optical system 2 (to the position shown by the dotted line in the figure), and when making monitor observations, it is inserted in the optical path of the photographic optical system 2. The path switching mirror 17 forms part of a television image receiving system 23. The television image receiving image system 23 comprises a mirror 24, a relay lens 25 and a CCD camera 26. The photoelectrically converted output of the CCD camera 26 is input to a processing circuit 27, and based on this photoelectrically converted signal, the processing circuit 27 outputs an image signal to a television monitor 28. Based on this image signal the television monitor 28 displays, for example, a fundus image 29.

The quick return mirror 18 is inserted in the optical path of the photographic optical system 2 when making observations through the eyepiece. The light beam from the fundus 22 is reflected by the quick return mirror 18, and passes via a mirror 31 and eyepiece lens 32 of the eyepiece optical system 30 to operator's eye 33. In this manner, the fundus 22, for example, of the subject's eye 20 may be observed.

To take color photographs, after the operator has conducted observations, he operates the photographic switch 104. This switches on the xenon lamp 5, the fundus 22 is illuminated, and the quick return mirror 18 is simultaneously withdrawn from the optical path of the photographic optical system 2. The light beam from the fundus 22 is thereby guided to the film 19, and film recording takes place.

When taking photographs by fluorescence under visible light, an exciter filter 34 for visible light-excited fluorescence is inserted between the mirror 9 and relay lens 8 of the illuminating optical system 1. When taking photographs by fluorescence under infra-red light, an exciter filter 35 for infra-red light-excited fluorescence is inserted. Further, when taking photographs by fluorescence under visible light, a barrier filter 38 for visible light-excited fluorescence is inserted between the holed mirror 12 and focusing lens 15 of the photographic optical system 2. When taking photographs by fluorescence under infra-red light, a barrier filter 37 for infra-red light-excited fluorescence is inserted.

Figure 3:
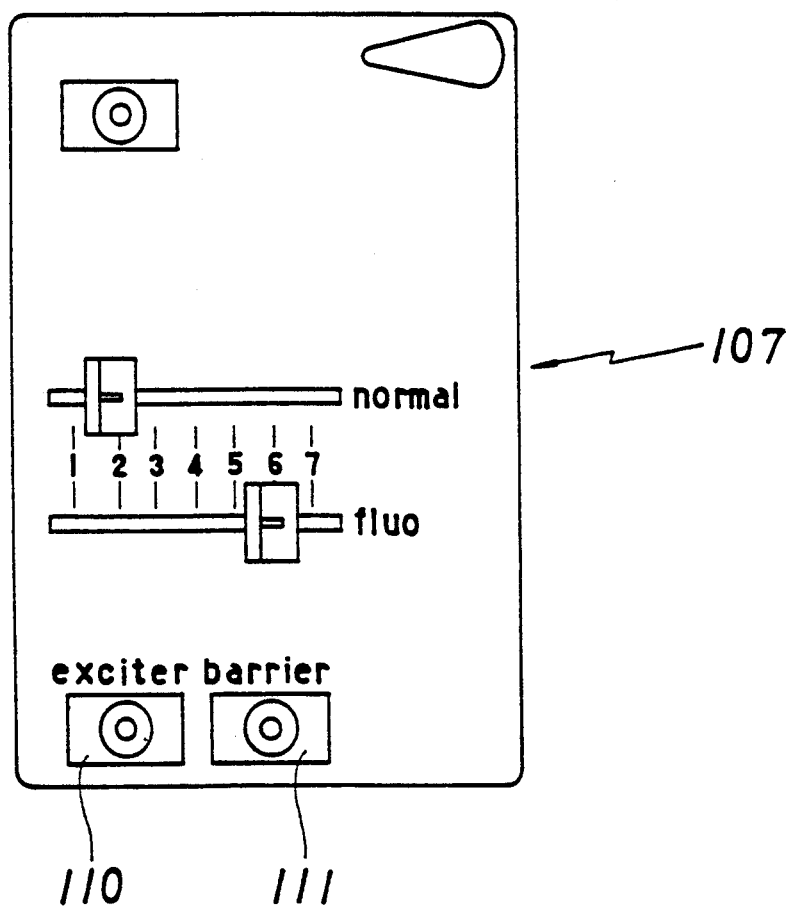

When making observations in the visible light-excited fluorescence photographic mode, and the brightness of the fluorescence emitted by the fluorescent agent has waned (in the later stage of fluorescence), an exciter filter withdrawal switch 110 provided on the control panel 107 is operated to withdraw the exciter filter for visible light-excited fluorescence from the optical path of the illuminating optical system 1 as shown in FIG. 3. Further, when a barrier filter withdrawal switch 111 is operated, the barrier filter for visible light-excited fluorescence is withdrawn from the photographic optical system 2.

Similarly, when making observations in the infra-red light-excited fluorescence photographic mode, and the brightness of the fluorescence emitted by the fluorescent agent has waned (in the later stage of fluorescence), the exciter filter withdrawal switch 110 is operated to withdraw the exciter filter for infra-red light-excited fluorescence from the optical path of the illuminating optical system 1. Further, when the barrier filter withdrawal switch 111 is operated, the barrier filter for infra-red light-excited fluorescence is withdrawn from the photographic optical system 2. These exciter filters and barrier filters are re-inserted in the illuminating and photographic optical systems by the operation of the photographic switch 104.

When taking photographs other than by fluorescence, the exciter filter 34 for visible light-excited fluorescence and the exciter filter 35 for infra-red light-excited fluorescence are withdrawn from the optical path of the illuminating optical system 1. When taking photographs by fluorescence, the barrier filter 36 for visible light-excited fluorescence and the barrier filter 37 for infra-red light-excited fluorescence are withdrawn from the optical path of the photographic optical system 2.

The action of the aforesaid camera will now be described.

FIG. 1 illustrates the apparatus in the mode for taking photographs other than by fluorescence. For this mode, the optical devices 13, 14 for correcting optical path length are inserted in the optical path of the photographic optical system 2. The operator observes the fundus 22 of the subject's eye 20 through the eyepiece lens 32, and operates the focusing control 106 so as to drive the focusing lens 15 and obtain a satisfactory focused image of the fundus. If necessary, the photographic switch 104 is operated to record the image of the fundus on the film 19. When taking photographs by fluorescence, the subject is first given an intravenous injection of a fluorescent agent. If photographs are to be taken by visible light excited fluorescence, for example, the operator operates a photographic mode selector switch, not shown, to select the visible light-excited fluorescent mode. Due to this operation, the optical device 13 for correcting optical path length is withdrawn from the optical path of the photographic optical system 2. At the same time, the exciter filter 34 for visible-light excited fluorescence is inserted in the optical path of the illuminating optical system 1, and the barrier filter 36 for visible-light excited fluorescence is inserted in the optical path of the photographic optical system 2. The barrier filter 36 for visible-light excited fluorescence and the optical device 13 for correcting optical path length are so constructed as to give the same optical path length taking account of wavelength differences, and the insertion of the barrier filter 36 in the optical path of the photographic optical system 2 therefore does not affect the path length of the system. Consequently, the operator does not have to re-focus the fundus image, and photographs can be taken with the system properly focused even if the barrier filter 36 is inserted in the photographic optical system while making observations. If the brightness of the fluorescence should decline so that good observations cannot be made, the switch 110 may be operated to withdraw the exciter filter 34 for visible-light excited fluorescence from the optical path of the illuminating optical system 1. The switch 111 may be operated to withdraw the barrier filter 36 for visible light excited fluorescence from the optical path of the photographic optical system 2, or both the exciter filter 34 and the barrier filter 36 may be withdrawn. These operations also cause the optical device 13 for correcting optical path length, to be re-inserted in the optical path of the photographic optical system 2. If a satisfactory fluorescent image is obtained by these procedures, the photographic switch 104 is operated. Due to this operation, the optical device 13 is withdrawn from the optical path of the photographic optical system 2, the exciter filter 34 is inserted in the illuminating optical system 1 and the barrier filter 36 is inserted in the photographic optical system 2. The xenon lamp tube 5 then operates. The barrier filter 36 for visible-light excited fluorescence and the optical device 13 for correcting optical path length both have an identical path length. The insertion of the barrier filter 36 in the optical path of the photographic optical system 2 therefore does not affect the path length of the system. Consequently, the operator does not have to re-focus the fundus image, and photographs can be taken with the system properly focused even if the barrier filter 36 is inserted in the photographic optical system while making observations. Further, an identical procedure is followed for taking photographs by fluorescence under infra-red light.

Observations in a non-fluorescent photographic mode may also be made with both the optical devices 13 and 14 withdrawn from the photographic optical system 2. Further, according to this embodiment, the photographic means was only a photographic film, but it may also consist of a means wherein photographic images are recorded on a magnetic disk.

In addition to the above-mentioned embodiments, when photographs are taken by visible light and a barrier filter for taking photographs by visible light is withdrawn from the optical path of the photographic system, only an optical device for taking photographs by visible light can be inserted in the optical path. When photographs are taken by infra-red light and a barrier filter for taking photographs by infra-red light is withdrawn from the optical path of the photographic system, only an optical device for taking photographs by infra-red light can be inserted in the optical path.

WHAT IS CLAIMED IS:

1. A fundus camera having an optical path for a photographic system and fluorescent photographing means for photographing a patient's eye fundus following intravenous injection of a fluorescent agent, the fundus camera comprising:

a visible light barrier filter disposed in the optical path when photographing the fundus according to fluorescence excited by illuminating the funds with visible light;

an infra-red light barrier filter disposed in the optical path in place of the visible light barrier filter when photographing the fundus according to fluorescence excited by illuminating the fundus with infra-red light; and an infra-red light optical device disposed in the optical path in place of the infra-red light barrier filter when observing the fundus, the infra-red light optical device being equivalent in optical path length to the infra-red light barrier filter.

2. A fundus camera having an optical path for a photographic system and fluorescent photographing means for photographing a patient's eye fundus following intravenous injection of a fluorescent agent, the fundus camera comprising:

a visible light barrier filter disposed in the optical path when photographing the fundus according to fluorescence excited by illuminating the fundus with visible light;

a visible light optical device disposed in the optical path in place of the visible light barrier filter when observing the fundus, the visible light optical device being equivalent in optical path length to the visible light barrier filter;

an infra-red light barrier filter disposed in the optical path in place of the visible light barrier filter when photographing the fundus according to fluorescence excited by illuminating the fundus with infra-red light; and an infra-red light optical device disposed in the optical path in place of the infra-red light barrier filter when observing the fundus, the infra-red light optical device being equivalent in optical path length to the infra-red light barrier filter.

3. A fundus camera according to claim 2, wherein the visible light optical device is disposed in the optical path of the photographic system when the infra-red light barrier filter is disposed in the optical path of the photographic system, and wherein the infra-red light optical device is disposed in the optical path of the photographic system when the visible light barrier filter is disposed in the optical path of the photographic system.

4. A fundus camera according to claim 3, wherein the visible light and infra-red light optical devices are inserted into the optical path of the photographic system to observe an image of the fundus.

5. A fundus camera according to claim 3, wherein the visible light and infra-red light optical devices are each a flat plate with parallel sides.

6. A fundus camera according to claim 2, wherein the visible light and infra-red light optical devices are inserted into the optical path of the photographic system to observe an image of the fundus.

7. A fundus camera according to claim 6, wherein the visible light and infra-red light optical devices are each a flat plate with parallel sides.

8. A fundus camera according to claim 2, wherein the visible light and infra-red light optical devices are each a flat plate with parallel sides.

9. A fundus camera according to claim 2, wherein the photographic system comprises a holed mirror and a focusing lens, the visible light and infra-red light optical devices being disposed between the holed mirror and the focusing lens.

* * * * *